US00PP08754P

United States Patent [19]

Meilland

[11] Patent Number: Plant 8,754

[45] Date of Patent: May 31, 1994

[54] HYBRID TEA ROSE PLANT NAMED 'MEILOSCOR'

[75] Inventor: Alain A. Meilland, Antibes, France

[73] Assignee: The Conard-Pyle Company, West Grove, Pa.

[21] Appl. No.: 61,068

[22] Filed: May 11, 1993

[51] Int. Cl.[5] ..... A01H 5/00

[52] U.S. Cl. ..... Plt./21

[58] Field of Search ..... Plt. 20, 21

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive very double long-lasting blossoms that are dark Currant Red suffused with Cardinal Red on the upper side, and dark Cardinal Red on the under side. The buds are elongated, and the stems tend to be very long, straight, and rigid. The plant exhibits an upright growth habit, forms somewhat small foliage, forms vigorous vegetation, and is particularly well suited for cut flower production. Additionally, the plant exhibits very good disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Meigrouge variety (U.S. Plant Pat. No. 7,383). The male parent (i.e., the pollen parent) was the Jelrocami variety (U.S. Plant Pat. No. 5,634). The parentage of the new variety can be summarized as follows:

Meigrouge×Jelrocami.

The seeds resulting from the above pollination were sown and 13 small plants were obtained which were physically and biologically different from each other. Selective study resulted in the identification of a single plant of the new variety.

It was found that the new variety of Hybrid Tea rose plant of the present invention possesses the following combination of characteristics:

(a) forms elongated buds,
(b) forms in abundance attractive long-lasting very double blossoms which are dark Currant Red suffused with Cardinal Red on the upper side, and dark Cardinal Red on the under side,
(c) forms very long straight and rigid stems,
(d) forms somewhat small foliage,
(e) exhibits vigorous vegetation,
(f) exhibits an upright growth habit,
(g) is particularly well suited for cut flower production, and
(b) is not particularly affected by cryptogamic diseases.

The new variety has been found to undergo asexual propagation by a number of routes, including budding, grafting, cuttage, etc. The characteristics of the new variety have been found to be strictly transmissible by such asexual propagation from one generation to another in France and in the United States.

The new variety has been named the Meiloscor variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during February while budded on *Rosa indica* understock and growing in greenhouses at Cap d' Antibes, France.

DETAILED DESCRIPTION

Figures 1, 2, 3, 4, 5, 6, 7, 8, 9, 10, 11, 12, 13, 14, 15, 16:
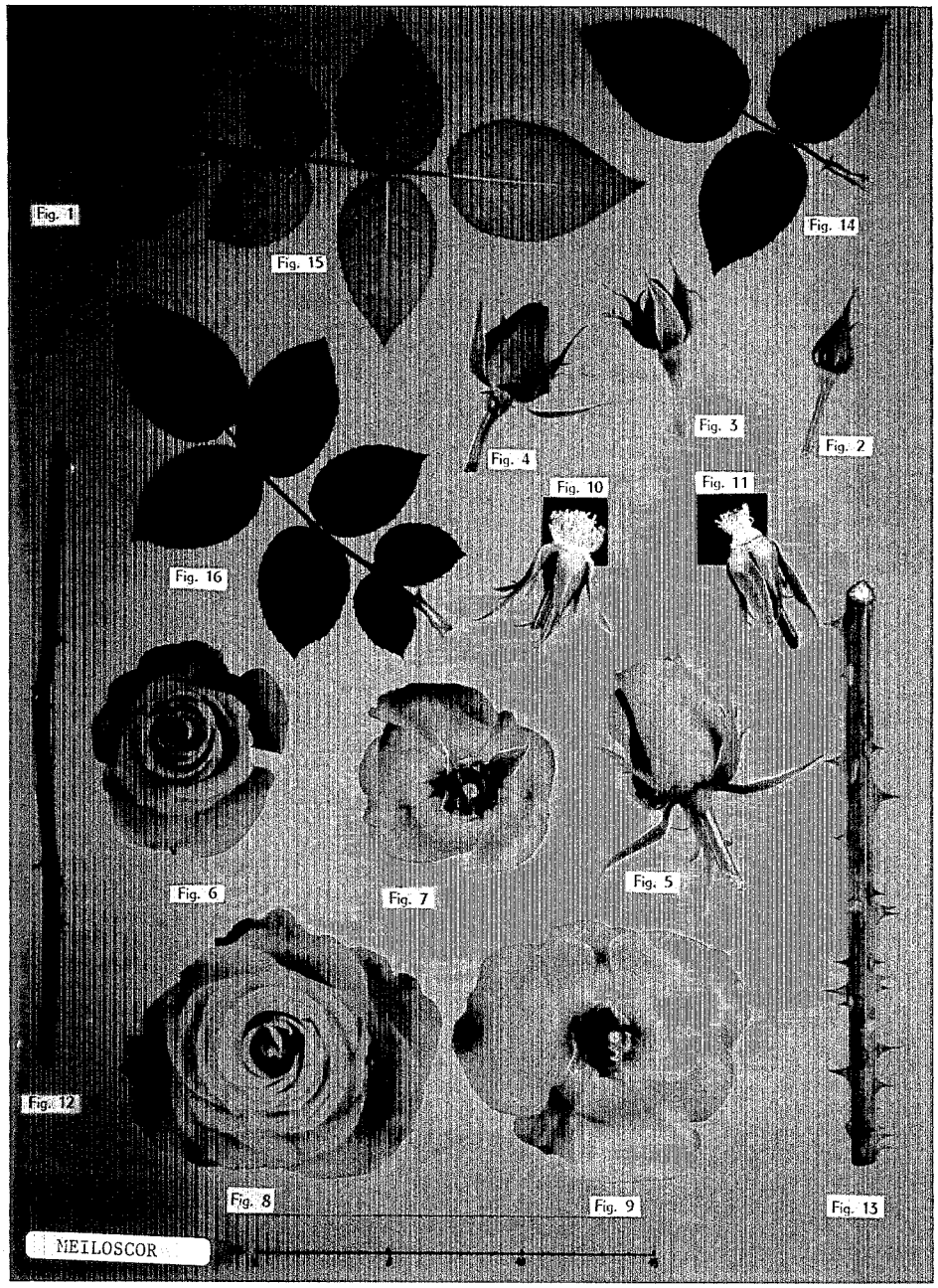
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets—plan view—upper surface.
FIG. 15 illustrates a specimen of a leaf with five leaflets—plan view—under surface.
FIG. 16 illustrates a specimen of a leaf with seven leaflets—plan view—upper surface.

The chart used in the identification of the colors is that of The Royal Horticultural Society (R.H.S. Colour Chart). The description is based on the observation of two year old plants made during February while budded on *Rosa indica* understock and growing in greenhouses at Cap d' Antibes, France. The coloration in common terms precedes reference to the chart.

Class: Hybrid Tea.

Plant:

*Height.*—When plants are cut to a height of 85 cm., flowering stems having lengths of approximately 70 to 100 cm. commonly are formed. When grown outdoors in fields at Wasco, Calif., at the end of one growing season, the plants commonly have a height of approximately 130 to 140 cm.

*Habit.*—Upright.

Branches:

Color.—Young stems: light green, Green Group 137C, more or less suffused with reddish coloration. Adult wood: medium green, Green Group 137B.

*Thorns.*—Size: medium to small. Quantity: average. Color: pinkish on young stems and greenish on mature wood.

Leaves:

*Stipules.*—Adnate, pectinate, wide and linear.

*Petioles.*—Upper surface: striped reddish brown on young foliage and medium green on adult wood with more or less glandular edges. Under surface: light green, and smooth.

*Leaflets.*—Number: 3, 5, and 7 (most often). Shape: elliptic to spear-shaped. Serration: single and regular. Texture: leathery. General appearance: not very dense, and semi-matte foliage. Color (young foliage): Upper surface: dark green, Green Group 137A. Under surface: grayish-green, Greyed-Green Group 191A, more or less stained with reddish coloration. Color (adult foliage): Upper surface: dark green, Green Group 139A. Under surface: grayish-green, Greyed-Green Group 191A.

Inflorescence:

*Number of flowers.*—Usually one single bloom per stem.

*Peduncle.*—Medium green, very long, and bears glandular acicules. The length is approximately 10 to 12 cm. on average.

Sepals.—Upper surface: tomentose, greenish in coloration. Under surface: light green, the outer sepals have edges which are more or less appendiculated.

*Buds.*—Shape: oblong. Length: approximately 4 cm. on average. Size: large. Color upon opening: Upper surface: dark Currant Red, Red Group 46A. Under surface: dark Cardinal Red, Red Group 53A.

*Flower.*—Shape: cup-like with parallel sides, very double. Diameter: approximately 13 to 14 cm. on average when fully open. Color (when opening begins): Upper surface: dark Currant Red, Red Group 46A. Under surface: dark Cardinal Red, Red Group 53A. Color (when blooming): Upper surface: Currant Red, Red Group 46A, and widely suffused with Cardinal Red, Red Group 53B. Under surface: medium Cardinal Red, Red Group 53C. Color (at end of opening): upper surface: Currant Red, Red Group 46A, and widely suffused with Cardinal Red, Red Group 53B, turning to light Cardinal Red, Red Group 53C. Under surface: light Cardinal Red, Red Group 53C. Fragrance: none. Lasting quality: long, when cut and placed in a vase. Petal number: approximately 37 to 46 on average. Petal shape: oval. Texture: very consistent. Petal drop: good. Shape: rounded with reflexive edges. Stamen number: approximately 91 on average. Anthers: normal, and ochre in coloration. Filaments: fuchsia with a straw-colored base, and of irregular heights. Pistils: approximately 90 on average. Stigmas: straw-colored. Styles: fucshia with a straw-colored base, tomentose near the base, more or less twisted, and of irregular heights. Receptacle: medium green in coloration, smooth, and in longitudinal section it is wide and in the shape of a pitcher at the dehiscence of the anthers.

Development:

*Vegetation.*—Very vigorous.

*Blooming.*—Abundant.

*Resistance to diseases.*—Very good.

*Aptitude to be forced.*—Good.

I claim:

1. A new and distinct variety of Hybrid Tea rose plant characterized by the following combination of characteristics:

(a) forms elongated buds,
(b) forms in abundance attractive long-lasting very double blossoms which are dark Currant Red suffused with Cardinal Red on the upper side, and dark Cardinal Red on the under side,
(c) forms very long straight and rigid stems,
(d) forms somewhat small foliage,
(e) exhibits vigorous vegetation,
(f) exhibits an upright growth habit,
(g) is particularly well suited for cut flower production, and
(h) is not particularly affected by cryptogamic diseases;

substantially as herein shown and described.

* * * * *

MEILOSCOR